United States Patent [19]
Reichert et al.

[11] Patent Number: 5,602,232
[45] Date of Patent: Feb. 11, 1997

[54] METHOD FOR PRODUCING METAL-INTERFERON-α CRYSTALS

[75] Inventors: Paul Reichert, Montville; Charles McNemar, High Bridge; Nagamani Nagahhushan; Tattanahalli L. Nagahhushan, both of Parsippany; Stephen Tindall, Madison; Alan Hruza, Hackettstown, all of N.J.

[73] Assignee: Schering Corporation, Kenilworth, N.J.

[21] Appl. No.: 356,021

[22] Filed: Dec. 14, 1994

Related U.S. Application Data

[63] Continuation-in-part of Ser. No. 24,330, Feb. 25, 1993, Pat. No. 5,441,734.

[51] Int. Cl.$^6$ .................................................. C07K 14/56
[52] U.S. Cl. .......................... 530/351; 530/419; 530/427
[58] Field of Search ............................... 530/351, 419, 530/427

[56] References Cited

U.S. PATENT DOCUMENTS

| | | | |
|---|---|---|---|
| 2,882,034 | 4/1959 | Peterson et al. | 514/3 |
| 4,315,852 | 2/1982 | Leibowitz et al. | 424/85.4 |
| 4,672,108 | 6/1987 | Kung et al. | 530/351 |
| 4,853,218 | 8/1989 | Yim et al. | 424/85.7 |
| 4,871,538 | 10/1989 | Yim et al. | 424/85.7 |
| 5,441,734 | 8/1995 | Reichert et al. | 530/351 |
| 5,460,956 | 10/1995 | Reichert et al. | 530/351 |

FOREIGN PATENT DOCUMENTS

| | | |
|---|---|---|
| 0281299 | 9/1988 | European Pat. Off. . |
| WO91/18927 | 12/1991 | WIPO . |
| 9419373 | 9/1994 | WIPO . |

OTHER PUBLICATIONS

T. L. Nagabushan, et al. Characterization of Genetically Engineered α–2 Interferon, *Interferon: Research and Regulatory Consideration*, pp. 78–88 (1982).

David L. Miller et al. Crystallization of Recombinant Human leukocyte Interferon A, *Science* 215:689–690 (Feb. 5, 1982).

C. Weissmann, et al., Structure and Expression of human IFN–αgenes, *Phil. Trans. R. Soc. Lond.* B299, 7–28 (1982).

Alexander McPherson, Preparation and Analysis of Protein Crystals. Hohn Wiley & Sons pp. 102–104. (1982).

David Olis et al. "Protein Crystallization": pp. 646–659; Guide to Protein Purification (Academic Press 1990).

Matsuda et al. "New Crystal Form of Recombinant Murine Interferon–β" *J. Biol. Chem* 264 (23): 13381–13382 (Aug. 1989).

Sano et al. "Crystallization of physiologically active proteins . . . " *Nippon Kessho Seicho Gakkaishi* 16(1):52–60 (1989).

Senda et al. "Three-dimensional Crystal Structure of Recombinant Murine Interferon–β" *The EMBO* 11(9):4193–3201 (Sep. 1992).

Lai et al. "Structure/function studies of murine interferon–α1 using site–directed mutagenesis followed by in vitro synthesis" *Antiviral Res.* 18: 65–76 (May 1992).

Waine et al., "Structure–Function Study of the Region Encompassing Resides 26–40 of Human Interferon–α4: Identification of Rediudes Important for Antiviral and Antiproliferative Activities" *J. Interfer. Res.* 12:43–48 (Feb. 1992).

Zav'yalov et al. "Theoretical analysis of conformation and active sites of interferons" *Immuno. Lett.* 22: 173–182 (Jul. 1992).

Senda et al. "Three-dimensional Structure of Recombinant Murine Interferon–β" *Proc. Japan Acad* 66(4) Ser B::77–80 (1990).

*Primary Examiner*—John Ulm
*Assistant Examiner*—Christine Saoud
*Attorney, Agent, or Firm*—Paul G. Lunn

[57] ABSTRACT

A method for producing a crystalline zinc interferon (IFN) α-2 comprising forming a soluble solution of IFN α-2 and a metal acetate salt under condtions wherein supersaturation and metal alpha interferon crystals occur.

17 Claims, 1 Drawing Sheet

METHOD FOR PRODUCING METAL-INTERFERON-α CRYSTALS

The present application is a continuation-in-part of U.S. application Ser. No. 08/024,330 filed Feb. 25, 1993, now U.S. Pat. No. 5,441,734.

BACKGROUND OF THE INVENTION

The present invention is in the field of protein crystallization and in particular protein crystallization of interferons.

The human interferon alphas are a family of proteins comprising at least 24 subspecies, Zoon K. C., Interferon 9:1 (1987), Gresser I., ed. Academic Press, N.Y. They were originally described as agents capable of inducing an antiviral state in cells but are known as pleiotropic lymphokines affecting many functions of the immune system, Opdenakker, et al., *Experimentia* 45:513 (1989). Apart from their in vitro biological activities the human interferon alphas are currently used for several indications, e.g., hairy cell leukemia, Kaposi's Sarcoma, venereal warts, hepatitis B and hepatitis C.

Interferon alpha-2b is prepared as a purified sterile, lyophilized recombinant interferon formulation. An example of a commercially available interferon alpha-2b is INTRON A® produced by Schering-Plough Corporation, Kenilworth, N.J. The demand for highly purified and crystalline forms of interferon alpha, especially the recombinant type alpha-2b, is of foremost importance for structure elucidation as well as for formulation of various dosage forms including the development of controlled release formulations.

Two forms of crystalline human interferon alpha have been reported, namely from Miller et al., *Science*, 215:689 (1982); Kung et al., U.S. Pat. No. 4,672,108; Weissmann, The Cloning of Interferon and other Mistakes, In: Interferon 1981, Ian Gresser, ed., Academic Press, N.Y., 101–134; Weissmann, *Phil. Trans. R. Soc. Lond.* B299:7 (1982); Nagabhushan, et al., 'Characterization of Genetically Engineered alpha-2 Interferon', In: *Interferon: Research Clinical Application and Regulatory Consideration*, Zoon et al., Elsevier, N.Y. 79 (1982). These publications describe methods for crystallizing interferon alpha-2 in polyethylene glycol at low temperature or in a phosphate buffer solution by adjusting the pH or temperature. The Miller et al. article also mentions crystalline alpha-2 in a "prismatic form". Conditions for producing monoclinic prismatic crystals of interferon alpha-2b from solutions of ammonium sulfate in vapor diffusion hanging drop experiments at 22° C. are disclosed in International Patent Application No. PCT/US 91/03660.

IFN-alpha is generally administered either by subcutaneous or intravenous injection usually in hospital or clinical settings. IFN-alpha has a serum half-life of 2–6 hours when injected subcutaneously or minutes when injected intravenously, and characteristically shows a "burst" or a "pulse" (i.e., a rapid blood serum level rise followed by a rapid blood serum level clearance) profile when blood levels are measured over time. Thus frequent administration of doses of the protein must be made to maintain a therapeutically effective blood serum concentration of the drug. There are clinical situations when it may be therapeutically more advantageous to develop an IFN-alpha formulation in which the protein is continuously released into the blood stream so that the serum concentration of the protein reaches a plateau and remains at that level for a period of time. This is an example controlled release formulation.

To date none of the known crystalline IFN-alphas have shown properties desirable for a controlled drug delivery system, in particular, limited solubility at 37° C. and stability in a 'Generally Recognized as Safe' (GRAS) category formulation suitable for injection. There are a number of potential advantages of a controlled release therapeutic. Primarily, controlled release drugs can be administered at lower effective doses which improves their safety while maintaining or improving their efficacy. New therapeutic indications can be explored because prolonged bioavailability offers the opportunity for increased biodistribution to enhance tissue and organ penetration.

There is thus a need for a controlled-release formulation of IFN-alpha.

SUMMARY OF THE INVENTION

The present invention fills this need by providing for a method for producing a crystalline metal-interferon (IFN) α-2.

In one embodiment of the present invention a method is provided for producing crystalline metal-IFN α-2 comprising forming a solution of metal acetate and IFN α-2, and warming the solution to a temperature wherein crystalline metal-IFN α-2 is formed.

In another embodiment a method is provided for producing crystalline metal-IFN α-2 comprising forming a first solution of IFN α-2 and a metal acetate salt, equilibrating the first solution against a second metal acetate salt, and warming the equilibrated solution to a temperature trader conditions to produce crystalline metal IFN α-2.

In another embodiment a method is provided for producing crystalline metal-IFN α-2 comprising of forming a first solution containing a metal acetate salt and IFN α-2, wherein the metal acetate salt is present at an initial concentration of 10 mM to 50 mM, and the IFN α-2 is present at an initial concentration of from 5 to about 80 mg/ml; and equilibrating the IFN α-2 solution against a second solution containing a metal acetate salt wherein the metal acetate salt is present at a higher concentration in the second solution than the concentration of the metal acetate salt is in the first solution.

DETAILED DESCRIPTION OF THE INVENTION

Figure 1:
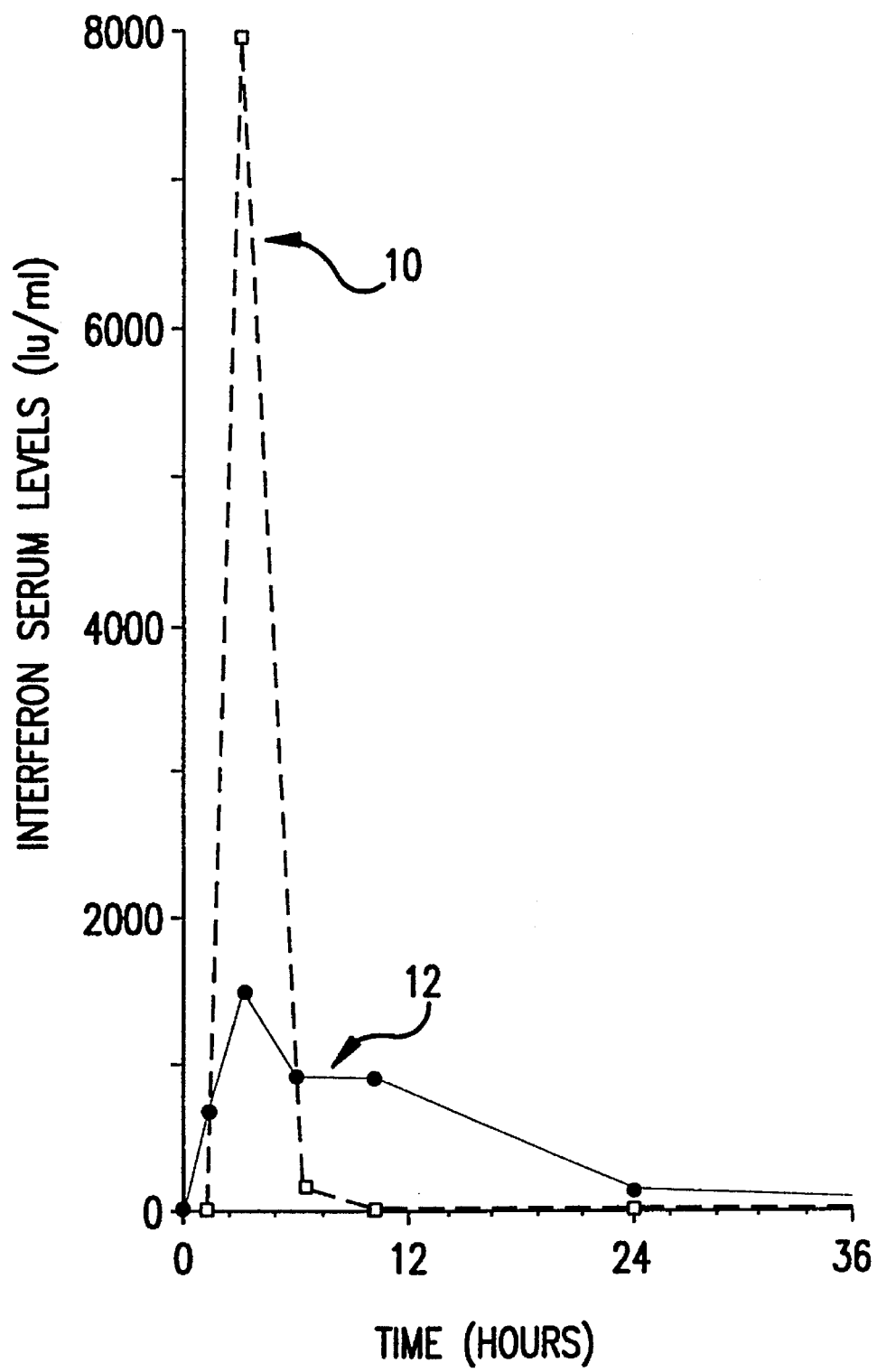
FIG. 1 depicts serum blood level of Interferon alpha-2b in phosphate buffer solution, graph 10, and of crystalline zinc interferon alpha-2b as a function of time injected by means of a protamine sulfate vehicle, graph 12.

The present invention relates to new crystalline morphologies of metal complexes of IFN-alpha. In particular, crystalline interferon complexes with zinc and cobalt are disclosed. These crystals have desirable solubility properties for use in drug delivery systems, which include limited solubility at 37° C., particle range <200 μm and stability at room temperature in solutions suitable for injection. Using a single subcutaneous injection of 34 ×10$^6$ IU of crystalline zinc-IFN-alpha-2b suspension into Cynomolgus monkeys, the measured elimination serum half-life was 12 hours as compared to 2–3 hours for the non-crystallized form INTRON A® (Schering-Plough, Kenilworth, N.J.) of IFN-alpha-2b. This is a 4–6 fold increase in serum half-life.

Supersaturated solutions of metal-interferon complexes can be induced to crystallize by several methods such as vapor diffusion, liquid diffusion, constant temperature and temperature induction or a combination thereof. Crystallization only occurs under narrow conditions of protein concentration, buffer concentration, metal ion concentration and temperature. These designated conditions for supersaturation can be obtained by vapor diffusion (hanging drop method), liquid diffusion (dialysis and ultrafiltration) at constant temperature between 4° to 22° C. or via temperature induction method (temperature raised from 4° to 22° C. over time). Preferably the metal salts used to complex with the interferon alpha-2b are salts of cobalt or zinc and the equilibration is carried out by temperature induction or by a combination of temperature induction and liquid diffusion.

The solution of IFN-alpha-metal complex contains a metal acetate salt. The metal acetate salt is preferably selected from zinc, cadmium, potassium, lithium, magnesium and cobalt more preferably it is zinc acetate and this solution is induced to crystallize either by a constant temperature method or a temperature induction method. In the case of vapor diffusion and liquid diffusion experiments, the solution is preferably equilibrated against a more concentrated zinc or cobalt acetate solution. Equilibration refers to the process in which the solvent of one solution, having a lower concentration of salt, osmotically diffuses into the solution of a second solution having a higher concentration of salt in an attempt to bring the concentrations of the salt in the two solutions to equilibrium. The acetate salt is preferably present in the crystalline IFN-alpha-2 solution at the time crystals begin to form in a concentration of from about 60 mM to about 140 mM, more preferably in a concentration of from about 80 mM to about 100 mM acetate salt. As noted below, the concentration of acetate salt at the start of the equilibration procedure will be lower, i.e., from about 20 mM to about 70 mM in the case of a vapor diffusion or liquid diffusion experiment.

Preferably, the IFN-alpha-2 is interferon alpha-2b and is more preferably human, recombinant interferon alpha-2b. In one embodiment, the material is interferon alpha-2b having the amino acid sequence shown in Sequence ID NO: 1.

IFN-alpha-2a may also be employed. The primary amino acid sequence of interferon alpha-2a differs from the sequence of IFN-alpha2b by the replacement of lysine for arginine at residue 23.

The acetate salt solution of interferon alpha-2 preferably includes a buffer having a pH of 5.0 to 7.0 more preferably from 5.5 to 6.5, such as a 35 mM sodium acetate, pH 6.0 buffer solution.

As noted above, the method of the present invention involves preparing a metal-IFN-alpha-2 soluble complex which under designated conditions of supersaturation crystallization occurs. Conditions for supersaturation can be reached using several crystallization methods such as vapor diffusion, liquid diffusion at constant temperature and temperature induction or a combination thereof. In a vapor diffusion method, a zinc-IFN-alpha-2 complex is equilibrated against an acetate salt solution that will cause the zinc-IFN-alpha-2 solution to become supersaturated and form interferon alpha-2 crystals at constant temperature. In a liquid diffusion method, a metal-IFN-alpha-2 complex in a metal acetate buffered solution is dialyzed against a higher concentration of the metal acetate buffered solution at constant temperature. In a temperature induction method, a metal-IFN-alpha solution in a metal acetate buffered solution is induced to crystallize by raising the temperature from 4° C. to 22° C.

Any suitable IFN-alpha-2 can be employed, e.g., IFN-alpha-2a and IFN-alpha-2b, more preferably human, recombinant IFN-alpha-2a (r-h-IFN-alpha-2a) or IFN-alpha-2b (r-h-IFN-alpha-2b). Commercially available IFN-alpha-2 preparations are available from Hoffmann-La Roche (ROFERON®) and Schering-Plough (INTRON A®). Mixtures of pure interferons including IFN-alpha 2 are available from Burroughs-Wellcome Corporation (WELLFERON®). In view of the high degree of sequence homology in the human IFN-alphas, the method of the present invention should be applicable for each subspecies.

The human IFN-alpha-2 subspecies may be obtained through recombinant DNA technology or may be purified from natural sources (e.g. human peripheral blood lymphocytes, human lymphoblastoid cell lines), for example, as described in Pestka, et al., *Ann. Rev. Biochem.*, 56:727 (1987). A preferred IFN-alpha-2 is r-h-IFN-alpha-2b having the amino acid sequence of SEQ ID NO: 1.

Natural human IFN-alphas have been purified from several cell sources including leukocytes isolated from whole blood, neonatal fibroblasts, lymphoblastoid and various leukemic cell lines. The first clinically available preparation of human leukocyte interferon was developed by K. Cantell and associates in Finland, in which centrifuged blood from normal donors is primed with interferon, induced to produce IFN-alpha by addition of Sendai virus and centrifuged. The resulting supernatant is precipitated with potassium thiocyanate, extracted with ethanol, pH precipitated, and dialyzed against phosphate buffered saline to produce purified IFN-alpha, K. E. Morgensen, et al., *Pharmacol. Ther.* 1:369 (1977).

Recombinant IFN-alphas have been cloned and expressed in E. coli by several groups, for example, C. Weissmaim, et al. *Science* 209:1343 (1980). The purification of recombinant IFN-alphas has been described by several groups using a combination of chromatographic steps such as ammonium sulfate precipitation, dye affinity chromatography, ion exchange and gel filtration, for example, as described in Weissmann, C., *Phil R. Soc.* (London), b299:7 (1982). An alternative approach for purifying recombinant IFN-alphas employs immunoaffinity chromatography with an immobilized antibody, P. P. Trotta et al., *Developments in Industrial Microbiology* 72:53 (Elsevier, Amsterdam 1987). For a review of available purification schemes used for recombinant alpha interferons, see T. L. Nagabhushan and P. P. Trotta, *Ulmann's Encyclopedia of Industrial Chemistry* A14, VCH: 372 (Weinheim, Federal Republic of Germany 1989). Preferably, the IFN-alpha-2b used is purified by a conventional purification process described in *Ullmann's Encyclopedia of Industrial Chemistry*, followed by reverse phase high performance chromatography.

Suitable methods of vapor diffusion for crystallizing IFN-alpha include using drops, e.g., hanging or sandwiched droplets. Vapor equilibration of an acetate salt solution of metal IFN-alpha-2 can be effected against a second acetate salt solution that has a higher concentration of the acetate salt than the first solution. Preferably, the equilibration occurs slowly, e.g., from over 1 hour to 30 days.

Large scale crystallization may be accomplished by other methods similar to vapor diffusion to establish supersaturation, namely, liquid diffusion, e.g., dialysis and ultrafiltration. Crystallization can also be induced by temperature induction, where non-crystalline suspensions or solutions of metal-interferon become supersaturated upon raising the temperature and subsequently nucleation and crystal formation occurs. Also a combination of methods can be envisioned to establish supersaturation for example diffusion in combination with temperature induction. In clinical manufacturing, large scale crystallization can be used as a purification or concentration step.

The final concentration of the IFN-alpha-2 in the acetate salt solution at the point of crystallization, i.e., at the point of first crystal formation, can range from about 5 to about 80 mg/ml. More preferably, the concentration of IFN-alpha-2 is from about 5 to about 50 mg/ml. Preferably, the IFN-alpha-2 starting concentration is about 40 mg/ml.

In the vapor diffusion method, the concentration of the metal acetate salt in the IFN-alpha-2 solution at the initial stage prior to the start of crystallization can range from about 10 to about 70 mM. More preferably, the concentration of the metal acetate salt is from about 20 to about 45 mM in the interferon alpha-2 solution. In the counter solution at the start of the crystallization procedure, the concentration of acetate salt is from about 60 to about 140 mM, more preferably, from about 80 to about 100 mM.

The pH of the IFN-alpha-2 solution and the counter acetate salt solution is preferably controlled in the range of from about 4.0 to about 7.0, more preferably from about 5.5 to about 6.5. Any suitable non-metal chelating buffer can be employed for this purpose. For example, sodium acetate, HEPES (N-2-hydroxyethylpiperazine-N'-2-ethanesulfonic acid) and MES (2-[N-Morpholino]ethanesulfonic acid) buffers can be employed.

Crystallization preferably is performed under a controlled temperature gradient for vapor diffusion and liquid diffusion methods. The temperature is preferably in the range of from about 7° to about 22° C., more preferably from about 6° to about 14° C. with nucleation generally being observed at about 9° C. for vapor diffusion.

For temperature induction methods, alpha interferon is placed in a metal acetate salt solution and the temperature of the solution is preferably raised from 1° C. to 40° C. over a time period ranging from instantaneously to several days. The temperature is preferably raised from 4° C. to 22° C. over 1 to 10 days in a linear gradient. More preferably from 4° C. to 18° C. over 1 to 10 days. The initial concentration of the alpha interferon is preferably 5–80 mg/ml of solution, more preferably 20–40 mg/ml. The initial concentration of metal acetate salt, which is preferably zinc acetate, is preferably 70–120 mM, more preferably 80–100 mM. The initial pH of the solution is preferably 5.5–6.2, more preferably 5.9–6.1.

A preferred method of the present invention is to produce crystalline metal IFN-alpha-2 by combination of liquid diffusion and temperature induction. According to this method, a solution of IFN α-2 and metal acetate is formed which results in a metal-IFN α-2 complex being formed. This solution is then dialysed against a second metal acetate solution at a pH higher than the pH of the first solution. The resultant metal acetate IFN α-2 solution is then gradually warmed under conditions to produce crystalline metal-IFN α-2.

In this method preferably an IFN α-2 solution is first formed. The concentration of IFN α-2 is 5–80 mg/ml of solution, preferably about 40 mg/ml. This solution is then dialysed to equilibrium against a metal acetate solution having a pH which allows the IFN α-2 and metal acetate to form a homogenous solution. Preferably the pH of the metal acetate solution is greater than or equal to about 4.0 and less than 6.0. The most preferred pH is 5.0.

The resultant dialysed IFN α-2 solution is then dialysed against a second metal acetate solution which has a higher pH than the first metal acetate solution. Preferably the pH of the second metal acetate solution is 5.5–6.2. The preferred pH is 6.0. This step allows for optimal conditions for crystallization by temperature induction.

The concentration of zinc acetate in each of the zinc acetate solutions should range from about 70 mM to 120 mM. The preferred concentration is 90 mM. The solutions should be made and dialysed at a constant temperature of 1° to 7° C.

The temperature of the resultant solution is then increased at a linear temperature gradient to a point at which crystals are formed. The initial temperature of the IFN α-2-metal acetate solution should be from about 1° to 7° C. The temperature of the solution is then gradually raised to a temperature ranging from 10° to 40° C. Preferably the temperature of the solution should be raised to a point ranging from 14° to 18° C.

After the maximum temperature is reached, it may be necessary to maintain the temperature of the solution at the maximum temperature for a period of time before crystals are formed. Typically this length of time can range from hours to days. Usually the incubation lasts for a matter of hours before crystallization is observed.

The crystalline IFN-alpha-2 prepared by the methods of the invention will form the basis for various pharmaceutical formulations. For example, the crystalline IFN-alpha can be employed in a controlled release formulation, e.g. a depot preparation for subcutaneous, intramuscular, or intralesional injections capable of releasing the equivalent of a daily dose of 0.1–1.0 μg/kg body weight.

A depot preparation employing crystals prepared by the methods of the invention should exhibit considerably slower rate of dissolution than a formulation containing the prior art crystals produced at the lower temperature of 4° C. In particular, ambient temperature (22° C.) crystals of the present invention are less temperature sensitive than crystals that require a lower temperature of formation. Preparations can contain a physiologically effective amount of the crystalline interferon alpha-2 in association with a conventional pharmaceutically acceptable carrier. One can envision using the controlled release effects of crystalline proteins in combination with other controlled release technologies such as microencapsulation. For example, crystalline proteins can be entrapped in Poly[dl-lactic-coglycolic] acid or liposomes.

EXAMPLES

The following examples are included to illustrate but not to limit the present invention.

The IFN-alpha-2 employed in the following examples was recombinant human interferon alpha-2b expressed in *E. coli* as described in Weissmann, et al. *Science*, 209:1342(1980). The cells were cultured, harvested and extracted as previously reported in Leibowitz, P. et al., US Pat. No. 4,315,852. The resulting extract was purified by a combination of conventional purification steps: ethanol extraction, matrix gel blue ligand affinity chromatography, ion exchange and gel filtration chromatography. The resulting purified IFN-alpha-2b preparation was dialyzed against either USP grade water or 0.1% trifluoroacetic acid solution and lyophilized as either the free base or trifluoroacetate salt respectively.

Example 1

Production of Crystalline Zinc IFN-alpha-2b having a Monoclinic Morphology

Using an automated crystallization system as disclosed in Kenyon et al., U.S. patent application Ser. No. 07/822,504 filed Jan. 17, 1992, International Patent Application No. PCT/US92/08296 filed Oct. 6, 1992, 6 μl droplets containing 20 mg/ml of IFN-alpha-2b in 17 mM sodium acetate, 17 mM zinc acetate, pH 5.5 were hung from the upper cover of a siliconized crystallization chamber. The upper plate was placed on the greased lower assembly of the crystallization chamber over a well containing 1 ml of 35 mM sodium acetate, 35 mM zinc acetate, pH 5.5. Large monoclinic crystals were evident from 5–6 days after incubation at 22° C.

Example 2

Production of Crystalline Zinc IFN-alpha-2b having a Monoclinic Morphology

In an alternative procedure, crystalline zinc IFN-alpha-2b having monoclinic morphology was produced. In this procedure, the zinc IFN-alpha-2b crystallization condition consisted of a 10 µl droplet containing 20 mg/ml IFN-alpha-2b in 2.5 mM sodium acetate, 37.5 mM zinc acetate, pH 6.1 hung from an 18 mm circular siliconized cover slide. The crystallization chamber, containing 1 ml of 5 mM sodium acetate, 75 mM zinc acetate, pH 6.1, was sealed to the siliconized cover slide by a bead of high vacuum grease around the rim of the crystallization chamber, thus suspending the hanging droplet above the crystallization chamber and above the acetate salt solution. Large monoclinic crystals were produced within 5–6 days after incubation at 12° C.

Example 3

Production of Crystalline Zinc IFN-alpha-2$b$. having a Monoclinic Morphology

In an alternative procedure, crystalline zinc IFN-alpha-2b having monoclinic morphology was produced. In this procedure, a 10 µl drop containing 20 mg/ml IFN-alpha-2b in 45 mM zinc acetate, pH 6.1 was suspended from the siliconized cover slide. The crystallization chamber contained 1 ml of 90 mM zinc acetate, pH 16.1 and was sealed with high vacuum grease to the cover slide suspending the hanging droplet above the crystallization chamber and above the zinc acetate solution. Large monoclinic crystals were produced within 5–6 days after incubation at 12° C.

Example 4

X-Ray Diffraction Data of Monoclinic IFN-alpha2$b$

For X-ray studies, IFN-alpha-2b monoclinic crystals produced according to the process of Example 1 were mounted in glass capillaries at 22° C. using $CuK_\mu$ radiation from a Rigaku RU-300 rotating anode generator operating at 40 kV and 100 mA. The native data set was collected on a Nicolet X-100 A area detector using the same radiation source.

The crystals were stable to X-ray diffraction analysis and diffracted to about $2.7 \times 10^{-10}$ m (Å) resolution, but the data became much weaker at about $3.2 \times 10^{-10}$ m (Å) resolution. Different batches of crystals were subjected to X-ray analysis and gave consistent results with respect to morphology. The crystals index in space group $P2_1$ with cell parameters $a=63.1\times10^{-10}$ m (Å), $b=76.6 \times 10^{-10}$ m(Å), $c=151.4\times10^{-10}$ m (Å), $\alpha=90°$, $\beta=91.2°$ and $\gamma=90°$. This is the first report of a metal alpha interferon having a monoclinic morphology.

Example 5

Liquid Diffusion Crystallization Method (plates)

In order for a crystalline suspension to have utility in a controlled release application, it must be possible to manufacture crystals in the milligram to gram scale. The current vapor diffusion in hanging drop method is not applicable to crystallize proteins at this scale. Experiments were set up to crystallize IFN-alpha-2 using a bulk dialysis method which mimicked the vapor diffusion in hanging drop method. A 0.5 ml solution of IFN-alpha-2b (40 mg/ml), 35 mM sodium acetate, pH 5.5 was dialyzed using a microdialysis bag having a molecular weight cutoff of 5000 kD (Pope Scientific Inc., Menomonee Falls, Wis.) against 2.7 liters of 35 mM sodium acetate, pH 5.5 at 22° C. A zinc acetate solution (0.3M) buffered to pH 5.5 was added dropwise over a two day period at 22° C. The purpose of dropwise addition was to slowly raise the zinc acetate level to 35 mM in the IFN-alpha-2b solution. A precipitate in suspension was observed after 1–2 hours of zinc acetate solution addition. The suspension was monitored microscopically daily. After 2 weeks, a few plates were observed in the suspension. The number of plates in the suspension increased daily (average size;70 µm) until the suspension contained about 90% crystals after 3 weeks.

Example 6

Liquid-diffusion Crystallization Method (plates)

A 0.5 ml IFN-alpha-2b solution having a concentration of 40 mg/ml of IFN-alpha-2b in 35 mM sodium acetate, pH 5.5 was dialyzed using a microdialysis bag having a molecular weight cutoff of 5000 kD (Pope Scientific Inc., Menomonee Falls, Wis.) against 2.7 liters of a buffer solution comprised of 35 mM sodium acetate and 35 mM zinc acetate, pH 5.5. The resulting suspension was incubated at 22° C. for 3 weeks. Masses of plate crystals were evident from 3–4 weeks by microscopic inspection.

Example 7

Temperature Induction Crystallization Method (plates)

A 0.5 ml IFN-alpha-2b solution having a concentration of 40 mg/ml of IFN-alpha-2b in 35 mM sodium acetate, 35 mM zinc acetate pH 5.0 was adjusted to pH 6.0 using 1 M sodium hydroxide at 4° C. The resulting suspension was submerged in a refrigerated bath/circulator (model #RTE-110, Neslab Instruments, Inc., Newington, N.H.). The temperature of the water bath was increased to 22° C. using a linear gradient over 4 days. Masses of plate crystals were evident after 4 days by microscopic inspection.

Example 8

Production of Crystalline Zinc IFN-alpha-2b Using a Combination of Vapor Diffusion and Temperature Induction Methods Using a combination of vapor diffusion and temperature induction, crystalline zinc IFN-alpha-2b having monoclinic morphology was produced. In this procedure, a 10 µl droplet containing 20 mg/ml IFN-alpha-2b in 40 mM zinc acetate, pH 6.0 was suspended from a siliconized cover slide at 4° C. The crystallization chamber contained 1 ml of 80 mM zinc acetate, pH 6.0 and was sealed with high vacuum grease to the coverslide suspending the hanging droplet above the crystallization chamber. The entire chamber was transferred to an incubator in which the temperature was 12° C. Large monoclinic crystals were produced within 3–5 days after incubation at 12° C.

Example 9–14

Characterization

Studies were initiated to characterize the zinc IFN-alpha-2b crystals using physical biochemical methods to insure molecular integrity, protein zinc content and retention of biological activity after dissolution.

Example 9

Protein Assay

An aliquot of bulk zinc IFN-alpha-2b crystals produced by the procedure of Example 3 was dialyzed against 2 liters of 35 mM sodium acetate, pH 5.5 at 22° C. for 4 days to remove non-complexed zinc acetate. The suspension was centrifuged and the wash solution was removed with a Pasteur pipette. The washed crystals were redissolved in 8 M guanidine hydrochloride solution at 22° C. Protein concentration was determined by a modified Bradford assay using pure human IFN-alpha2b as a reference standard. Bradford assay: A modification of the standard Coomassie blue dye binding assay so that the absorbance is directly proportional to protein concentration. Details are in Bradford, M., *Anal. Biochem.* 72:248 (1976).

Example 10

HPLC

Analytical high performance liquid chromatography (HPLC) (Waters Ass., Milford, Mass.) was performed on an aliquot of redissolved IFN-alpha-2b crystals produced according to the procedure of Example 3. The sample was applied to a RAININ DYNAMAX® $C_4$ $300\times10^{-10}$ m (Å) column (4.6 ×250 mm) which was subsequently eluted with a linear gradient of acetonitrile, 27–72% in 0.1% trifluoroacetic acid over a 30 minute period. A Gilson variable wavelength detector set at 280 nm with a sensitivity of 0.02 absorbance units was used to monitor the eluate. The retention times and chromatographic profiles of both the redissolved crystal solution and the original IFN-alpha-2b preparation prior to crystallization were indistinguishable.

Example 11

SDS-Page Analysis

Crystals harvested from a vapor diffusion in hanging drop experiment according to the procedure of Example 1 were centrifuged and washed several times to remove any soluble IFN-alpha. The centrifuged pellet was dissolved in a buffer containing sodium dodecyl sulfate. The resulting solution was run on a 12% sodium dodecyl sulfate-polyacrylamide gel electrophoresis (SDS-PAGE), Laemmli, U.K. *Nature*, 227:680 (1970) vs. a sample of IFN-alpha-2b. There was no apparent change in the molecular weight of the dissolved crystals vs. the control IFN-alpha-2b samples. Based on these results, there was no evidence of chemical or enzymatic modification of the IFN-alpha-2b during the crystallization process or subsequent dissolution.

From the results of Examples 10 and 11 above, it can be concluded that no chemical changes or any denaturing of the protein took place during the crystallization or reconstitution.

Example 12

Physical Properties of Zinc IFN-alpha 2b

The properties of the crystals produced according to the procedure of Example 1 were probed for suitability in controlled release formulations by observing microscopically their stability at 37° C. (body temperature) and 4° C. Also, crystal stability was observed in a non-zinc buffer at different pH's over a period of 18 hours. The crystals were found to be stable for 24 hours at 37° C. and 4° C. and stable between pH 5.0–6.0. This differs from the characteristics of the previous crystalline IFN-alpha-2b preparations, especially the crystals from Nagabhushan, et al., 'Characterization of Genetically Engineered alpha-2 Interferon', In: *Interferon: Research, Clinical Application and Regulatory*, which dissolve readily above and below pH 6.0 as well as at 4° C. at pH 6.0.

Example 13

Molar Ratio of Complexed Zinc vs. Interferon Content

An experiment was designed to determine the molar ratio of complexed zinc vs. IFN-alpha-2b. An aliquot of bulk zinc-IFN-alpha-2b crystals produced according to the procedure of Example 3 was dialyzed against 2 liters of 35 mM sodium acetate, pH 5.5 for 4 days to remove non-complexed zinc acetate. An 8.0 M guanidine hydrochloride solution was added to the washed suspension to dissolve the complex. The resulting solution was assayed using a Bradford assay for protein content. A sample of the same suspension was submitted for a zinc assay based on atomic absorption analysis. A 3.1 to 1 molar ratio of zinc ions to IFN-alpha-2b was found. Analysis of subsequent batches of zinc-IFN-alpha-2b gave a ratio of from 2 to 4 moles of zinc ions per mole of IFN-alpha-2b.

Example 14

Cytopathic Effect Inhibition Assay

To determine if the crystalline IFN-alpha-2b retained its biological activity a cytopathic effect inhibition assay was carried out. The virus which was used was the Encephalomyocarditis virus (EMC), ATCC strain VR-129B, and was grown in monolayer cultures of Vero cells and stored frozen in Medium A. (Medium A is comprised of 950 ml of Minimum Essential Medium Eagle with Earle's balanced salt solution (Gibco Inc.), 100 ml fetal bovine serum, 36 ml of 7.5% sodium bicarbonate, 20 ml of 1M HEPES Buffer in saline, 20 ml of 200 mM L-Glutamine, and 10 ml of penicillin and streptomycin (10,000 unit of K-Penicillin/ml. and 10,000 µg streptomycin sulfate/ml). Confluent monolayers of FS-71 cells in tissue culture roller bottles were rinsed with Hank's balance salt solution and incubated at 37° C. for 10 minutes with a 2.5% trypsin solution. The trypsin solution containing the cells was diluted in Medium A such that the concentration of cells was $3.5\times10^5$ and used in the assay as described below.

Interferon Assay

The entire procedure for the anti-viral Bioassay was done in a 96 well microtiter plate. The samples to be tested were placed into the appropriate wells and serially diluted 1:2 across the plate. On each plate, 24 wells were filled with Medium A to serve as virus and cell controls. Additionally, a laboratory standard of interferon alpha-2b containing 600 IU/ml of Interferon alpha-2b was diluted to 1 IU/ml, the concentration level necessary to give a 50% protection level from viral cytopathology, was included in all assays so that the relative anti-viral activity of samples could be determined and compared across assays. Each well was then seeded with approximately $3.5\times10^4$ cells in 0.1 ml of Medium A. The plate was covered and incubated at 37° C., 5% $CO_2$ for 4 hours. All wells, except the cell control wells, received EMC virus at a concentration appropriate to induce 90–100% cytopathology in 16–18 hours post-infection which was approximately $1.54\times10^4$ plaque forming units. The plates were recovered and incubated at 37° C., 5% $CO_2$ until the virus control wells displayed a cytopathic effect (CPE) of at least 90%. The media from each well was aspirated and the cell monolayer was stained with 0.1 ml of crystal violet preparation for about 30 minutes. After the crystal violet was decanted, the plates were gently rinsed with water and allowed to air dry. The virus and cell control wells were scored from 1 to 4+(1 =<10% CPE and 4+=>90% CPE) by visual inspection of the monolayer with and without a microscope. Samples on test plates that showed appropriate control responses were then graded. The grading of each sample well consisted of visual examination and comparison by the standard wells. The 50% endpoint for samples is determined by direct comparison to the 50% endpoint for the standard by selection of the sample well(s) which match most closely. The shift in a sample's 50% endpoint as compared to that of the standard gives estimates of titer values relative to the standard. Therefore, a shift of X wells [X=(50% well No. for sample) −(50% well No. for standard)]translates to a potency of $2^x$ times the potency of the standard.

A detailed description of the assay is provided in S. Rubinstein, P. C. Familetti and S. Petska, *J. Virol.* 37:755 (1981).

Example 15

Controlled Release Potential of Zinc-Interferon alpha 2b in a Protamine Vehicle.

An in vivo experiment was devised to test the controlled release potential of the crystalline suspension in a GRAS formulation suitable for subcutaneous injection. Using IFN-alpha-2b produced according to the procedure of Example 7, a sterile zinc-IFN-alpha-2b crystalline suspension ($34 \times 10^6$ IU/dose) was prepared in 10 mM sodium acetate, 10 mM zinc acetate, 0.4 mM protamine sulfate, pH 5.5 buffer. This suspension was injected subcutaneously into the small of the back of two Cynomolgus monkeys. The interferon blood serum level was monitored as a function of time at 1, 3, 6, 10, 24, 48 and 72 hours using the cytopathic effect inhibition assay (CPE).

See graph 12 of FIG. 1 which shows the IFN-alpha mean serum level of the two monkeys determined by the CPE assay as a function of time.

Example 16

Control Study

The experimental results obtained in Example 15 differ from the present experiment in which non-crystalline IFN-alpha-2b was prepared in a normal saline phosphate buffer solution. A Cynomolgus monkey received a subcutaneous injection in the small of the back at a dosage of $50 \times 10^6$ IU/injection. The interferon levels in the blood serum were measured at 1, 3, 6, 10, 24, 48, and 72 hours. The data are shown graphically in graph 10 of FIG. 1 which shows the IFN-alpha serum level as determined by the CPE assay as a function of time.

From Examples 15 and 16, it can be concluded that the use of crystalline zinc IFN-alpha in a protamine vehicle results in a prolonged detectable level of IFN-alpha in the blood serum relative to the prior art IFN-alpha administration described in Example 16. Furthermore, the data supports the utility of zinc interferon crystalline suspension as a controlled release formulation. The crystalline complex can be manufactured in large quantities using a process based on bulk dialysis or temperature induction. This large scale process produces crystals in the 1–200 μm size which is desirable for an injectable product (can be injected with a tuberculin syringe).

TABLE 1

Pharmacokinetic Profile for Crystalline IFN Suspension vs. Non-Crystalline IFN in Monkeys

|  | FIG. 1 Graph 10 | FIG. 1 Graph 12 |
|---|---|---|
| Cmax | 8000 | 1500 |
| Tmax | 3 | 3 |
| AUC (tf) | 20225 | 16812 |
| tf | 6 | 24 |

TABLE 1-continued

| Cmax | IU/ml | Maximum plasma concentration |
|---|---|---|
| Tmax | hr. | Time of maximum plasma concentration |
| AUC(tf) | IU.hr/ml | Area under the plasma concentration-time curve from the time 0 to time of final measurable sample |
| tf | hr | Time of final measurable sample |

TABLE 2

Serum Level (CPE) vs. Time

| Time (hr) | FIG. 1 Graph 10 | FIG. 1 Graph 12 (mean) |
|---|---|---|
| 0 | 0 | 0 |
| 1 | 0 | 676 |
| 3 | 8000 | 1500 |
| 6 | 150 | 900 |
| 10 | 0 | 114 |
| 24 | 0 | 0 |
| 48 | 0 | 0 |
| 72 | 0 | 0 |

Example 17

Cobalt-Interferon alpha-2b Complex Crystals

Using an automated crystallization system as disclosed in Kenyon et al., U.S. patent application Ser. No. 07/822,504 filed Jan. 17, 1992, International Patent Application No. PCT/US92/08296 filed Oct. 6, 1992, a 6 μl droplet containing 20 mg/ml of alpha-2b interferon in 17 mM sodium acetate, 22 mM cobalt acetate, pH 4.6 was hung from the upper cover of a siliconized crystallization chamber. The upper plate was placed on the greased lower assembly of the crystallization chamber over a well containing 1 ml of 35 mM sodium acetate, 45 mM cobalt acetate, pH 4.6. Crystals were evident from 5–6 days after incubation at 22° C. upon microscopic inspection.

Example 18

Production of Crystalline Zinc IFN-alpha-2b Using Lithium Acetate in the Crystallization Buffer A 10 μl droplet containing 20 mg/ml IFN-alpha-2b in 37.5 mM zinc acetate, pH 6.1, 2.5 mM lithium acetate was suspended from the underside of a siliconized cover slide. The crystallization chamber contained 1 ml of 75 mM zinc acetate, pH 6.1, 5.0 mM lithium acetate and was sealed to the coverslide with high vacuum grease. Monoclinic crystals appeared in 5–6 days after incubation at 12° C.

Example 19

Production of Crystalline Zinc IFN-alpha-2b using Potassium Acetate in the Crystallization Buffer A 10 μl droplet containing 20 mg/ml IFN-alpha-2b in 37.5 mM zinc acetate, pH 6.1, 2.5 mM potassium acetate was suspended from the underside of a siliconized cover slide. The crystallization chamber contained 1 ml of 75 mM zinc acetate, pH 6.1, 5.0 mM potassium acetate and was sealed to the coverslide with high vacuum grease. Large monoclinic crystals appeared in 5–6 days after incubation at 12° C.

Example 20

Preparation of Crystalline Zinc IFN alpha-2b Using a Temperature Induction Method Forty (40) mg of lyophilized interferon alpha-2b was weighed out and rehydrated in 1 ml of USP grade water and filtered using a 0.2 μl filter. The solution was dialyzed in a (Pope) dialysis bag against 90 mM zinc acetate, pH 5.0 for 18 hours at 4° C., after which the solution was redialyzed in a (Pope) dialysis bag against 90 mM zinc acetate, pH 6.0 for 18 hours at 4° C. The solution was then transferred to a sterile glass vial and the temperature was increased from 4°–14° C. for 18 hours. At which time, masses of monoclinic crystals (53×55×80 micrometers) were observed.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

and the solution has an initial concentration of the metal acetate salt of from 70 mM to 120 mM; and warming the solution until supersaturation occurs and metal IFN α-2 crystals appear, wherein the solution has an initial temperature of from about 4° C., and the solution is warmed to a temperature of about 22° C.

2. The method of claim 1 wherein the pH of the solution is about 6.

3. The method of claim 1 wherein the temperature of the solution is increased to about 22° using a linear gradient over 4 days.

4. The method of claim 1 wherein the initial concentration of the metal acetate salt is about 90 mM.

What is claimed is:

1. A method for producing a crystalline metal interferon (INF)α-2 comprising:

forming an aqueous solution of IFN α-2 and a metal acetate salt at a pH of from about 5 to about 7, wherein the solution has an initial concentration of IFNα-2 of from 5 to about 80 mg of IFN α-2/ml of solution, the metal acetate salt is either zinc acetate or cobalt acetate, 5. A method for producing a crystalline metal-interferon alpha-2 (IFNα-2) comprising the following steps:

(a) forming a first aqueous solution containing IFNα-2 and a metal acetate salt, said metal acetate being either zinc acetate or cobalt acetate, and said first solution having a pH of between about 4 to 6 and wherein the IFNα-2 solution contains about 5–80 mg of IFNα-2/ml of solution and wherein the first solution has a temperature of about 4° C.;

(b) dialysing the first solution against a second aqueous solution containing metal acetate, wherein the metal acetate is either zinc acetate or cobalt acetate, wherein the second solution has a higher pH than the first solution, and wherein the second solution has a pH of about 5.5 to about 6.2; and (c) warming the dialysed IFNα-2 solution from a temperature of about 4° C. to 22° C. wherein crystalline metal-IFNα-2 is formed.

6. The method of claim 5 wherein the pH of the first solution is about 5.0.

7. The method of claim 5 wherein the second solution has a pH of about 6.0.

8. A method for producing crystalline zinc Interferon (IFN)α-2 comprising the following steps:

(a) forming a first aqueous solution of IFNα-2 wherein the IFNα-2 solution contains about 5–80 mg of IFNα-2/ml of solution wherein the solution is at a temperature of about 4 ° C.;

(b) dialysing the IFN α-2 solution against a second aqueous solution containing zinc acetate until equilibrium of zinc acetate is reached between the IFNα-2 solution and the second solution, wherein the second solution has a concentration of zinc acetate of 70 mM–120 mM and wherein the second solution has a pH greater than or equal to about 4 and less than about 6;

(c) dialysing the equilibrated IFNα-2 solution of step (b) against a third solution containing zinc acetate until equilibrium is reached, wherein the third solution has a higher pH than the second solution, wherein the third solution has a pH of between about 5.5 and 6.2 and wherein the third solution has a concentration of zinc acetate of 70 mM–120 mM; and (d) warming the equilibrated IFNα-2 solution of step (c) from about 4° C. to about 14° to 18° under conditions wherein crystalline zinc-IFNα-2 is formed.

9. The method of claim 8 wherein the IFN α-2 solution of step (a) contains about 40 mg of IFN α-2/ml of solution.

10. The method of claim 8 wherein the second solution and third solution each have a concentration of zinc acetate of about 90 mM.

11. The method of claim 8 wherein the second solution has a pH of about 5.0.

12. The method of claim 8 wherein the IFN α-2 solution is dialysed against the second solution at a temperature of about 1° to 7° C.

13. A method for producing crystalline zinc Interferon (IFN) α-2 comprising the following steps:

(a) forming a solution of IFN α-2 having a concentration of IFN α-2 of about 40 mg/ml of solution at a temperature of about 4° C.;

(b) dialysing at about 4° C. the IFN α-2 solution against a second solution containing zinc acetate having a concentration of about 90 mM, and a pH of about 5.0, until equilibrium is reached;

(c) dialysing at about 4° C. the equilibrated IFN α-2 of step (b) against a third solution containing zinc acetate at a concentration of about 90 mM at a pH of about 6.0 until equilibrium is reached; and (d) warming the equilibrated IFN α-2 solution of step (c) from a temperature of 4° C. to a temperature ranging from 12° –22° C. under conditions wherein crystalline zinc-IFN α-2 is formed.

14. The method of claim 13 wherein the equilibrated IFN α-2 of step (c) is warmed from a temperature of about 4° C. to a temperature ranging from 14° C. to about 18° C.

15. A method for producing a crystalline metal-interferon (IFN)α-2 comprising:

forming a first aqueous solution containing a metal acetate salt and IFNα2 at a temperature of about 1° to 4° C., wherein the metal acetate salt is present at an initial concentration of 10 mM to 50 mM, the first solution has a pH of from about 5 to about 7 and the IFNα-2 is present at an initial concentration of from 5 to about 80 mg/ml, and said metal acetate being either zinc acetate or cobalt acetate; and equilibrating the IFNα-2 solution against a second aqueous solution containing a metal acetate salt, said metal acetate salt being either zinc acetate or cobalt acetate, at a temperature ranging from 12° C. to 18° C. wherein the metal acetate salt is present at a higher concentration in the second solution than the concentration of the metal acetate salt is in the first solution.

16. The method of claim 15 wherein the initial concentration of the metal acetate salt in the second solution is from 20 to about 100 mM.

17. The method of claim 15 wherein the first solution is equilibrated against the second solution by either liquid diffusion or vapor diffusion.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 165 amino acid residues
( B ) TYPE: amino acid
( D ) TOPOLOGY: linear ( i i ) MOLECULE TYPE: peptide ( x i ) SEQUENCE DESCRIPTION: SEQ ID NO: 1:

| Cys | Asp | Leu | Pro | Gln | Thr | His | Ser | Leu | Gly | Ser | Arg | Arg | Thr | Leu | Met |
|---|---|---|---|---|---|---|---|---|---|---|---|---|---|---|---|
| | | | | 5 | | | | | 10 | | | | | 15 | |
| Leu | Leu | Ala | Gln | Met | Arg | Arg | Ile | Ser | Leu | Phe | Ser | Cys | Leu | Lys | Asp |
| | | | 20 | | | | | 25 | | | | | 30 | | |
| Arg | His | Asp | Phe | Gly | Phe | Pro | Gln | Glu | Glu | Phe | Gly | Asn | Gln | Phe | Gln |
| | | 35 | | | | | 40 | | | | | 45 | | | |
| Lys | Ala | Glu | Thr | Ile | Pro | Val | Leu | His | Glu | Met | Ile | Gln | Gln | Ile | Phe |
| | 50 | | | | | 55 | | | | | 60 | | | | |
| Asn | Leu | Phe | Ser | Thr | Lys | Asp | Ser | Ser | Ala | Ala | Trp | Asp | Glu | Thr | Leu |
| 65 | | | | | 70 | | | | | 75 | | | | | 80 |
| Leu | Asp | Lys | Phe | Tyr | Thr | Glu | Leu | Tyr | Gln | Gln | Leu | Asn | Asp | Leu | Glu |
| | | | | 85 | | | | | 90 | | | | | 95 | |
| Ala | Cys | Val | Ile | Gln | Gly | Val | Gly | Val | Thr | Glu | Thr | Pro | Leu | Met | Lys |
| | | | 100 | | | | | 105 | | | | | 110 | | |
| Glu | Asp | Ser | Ile | Leu | Ala | Val | Arg | Lys | Tyr | Phe | Gln | Arg | Ile | Thr | Leu |
| | | 115 | | | | | 120 | | | | | 125 | | | |
| Tyr | Leu | Lys | Glu | Lys | Lys | Tyr | Ser | Pro | Cys | Ala | Trp | Glu | Val | Val | Arg |
| | 130 | | | | | 135 | | | | | 140 | | | | |
| Ala | Glu | Ile | Met | Arg | Ser | Phe | Ser | Leu | Ser | Thr | Asn | Leu | Gln | Glu | Ser |
| 145 | | | | | 150 | | | | | 155 | | | | | 160 |
| Leu | Arg | Ser | Lys | Glu | | | | | | | | | | | |
| | | | | 165 | | | | | | | | | | | |